US005420009A

United States Patent [19]

Hartung et al.

[11] Patent Number: 5,420,009

[45] Date of Patent: May 30, 1995

[54] **DETECTION OF *XANTHOMONAS CAMPESTRIS* PV. CITRI BY HYBRIDIZATION AND POLYMERASE CHAIN REACTION ASSAYS**

[75] Inventors: John S. Hartung, Beltsville, Md.; Olivier P. Pruvost, Saint-Pierre, France

[73] Assignee: The United States of America as represented by the Secretary of Agriculture, Washington, D.C.

[21] Appl. No.: 72,282

[22] Filed: Jun. 9, 1993

Related U.S. Application Data

[63] Continuation-in-part of Ser. No. 855,804, Mar. 23, 1992, abandoned.

[51] Int. Cl.$^6$ ........................ C12Q 1/68; C12P 19/34; C07H 21/04; C12N 15/63

[52] U.S. Cl. ........................ 435/6; 435/91.2; 435/320.1; 536/24.32; 536/24.33

[58] Field of Search ........................ 435/6, 91.2, 320.1; 536/24.32, 24.33

[56] References Cited

U.S. PATENT DOCUMENTS 4,683,202 7/1987 Mullis .................................. 435/91

OTHER PUBLICATIONS

Pruvost et al. (1992, Apr.) Phytopathology 82: 485–490.

Goto et al., *Ann. Phytopath. Soc. Japan*, vol. 46, pp. 329–338 (1980).

(List continued on next page.)

*Primary Examiner*—Margaret Parr
*Assistant Examiner*—Lisa Arthur
*Attorney, Agent, or Firm*—M. Howard Silverstein; John Fado; Janelle S. Graeter

[57] ABSTRACT

*Xanthomonas campestris* pv. *citri* is a quarantine organism under United States and International law because of the serious disease of citrus, citrus bacterial canker disease, which is caused by the organism. We have cloned, in vector pUC9, a 4.2-kb BamHI fragment of plasmid DNA from a typical strain of this pathogen and demonstrated that this DNA fragment specifically identifies the pathogen. The procedure involves isolation and cultivation of the bacterium, chemical isolation of its DNA, digestion of the DNA by restriction endonucleases and analysis by Southern or dot blotting using the cloned DNA fragment as biotin-labeled hybridization probe. A subclone has been made from the original 4.2-kb BamHI fragment which has sensitivity and specificity equal or greater than the original clone and which is approximately 572 bp in length. All tested strains of the most virulent form of the pathogen, type A, have a BamHI fragment of 4.2-kb which hybridizes with either probe. Other less pathogenic forms of the bacterium have BamHI fragments greater than 20kb in size. Thus not only are all strains of the pathogen detected with this probe, but sub-pathovar assignment of unknown strains is also facilitated. Strains of *X. campestris* which cause another non-threatening disease of citrus, citrus bacterial spot disease, are not detected by the probes. This will allow rapid, sensitive and specific detection of the pathogen in groves or from commercial shipments of citrus.

In addition, oligonucleotide primers were designed, based on the nucleotide sequence of the 572-bp probe. The primers are effective in the amplification of DNA from the bacterium; thereby increasing both the specificity and sensitivity of detection methods.

24 Claims, 10 Drawing Sheets

OTHER PUBLICATIONS

Kado and Liu, *Journal of Bacteriology,* vol. 145 (3), pp. 1365–1373 (1981).

Civerolo and Fan, *Plant Disease,* vol. 66 (3), pp. 231–235 (Mar., 1982).

Civerolo E. L., *Journal Rio Grande Valley Horticultural Society,* vol. 37, pp. 127–146 (1984).

Civerolo, E. L., *Phytopathology,* vol. 75 (5), pp. 524–528 (1985).

Schoulties et al., *Plant Disease,* vol. 71 (5), pp. 388–395 (1987).

Denny, T. P., *Phytopathology,* vol. 78 (9), pp. 1186–1192 (1988).

Gabriel et al., *Molecular Plant–Microbe Interactions,* vol. 1 (2), pp. 59–65 (1988).

Gilbertson et al., *Phytopathology,* vol. 79 (5), pp. 518–524 (1989).

Hartung and Civerolo, *Phytopathology,* vol. 79 (9), pp. 793–799 (1989).

Schaad et al., *Phytopathology,* vol. 79 (8), pp. 903–907 (1989).

Thompson et al., *Phytopathology,* vol. 79 (3), pp. 311–314 (1989).

Egel et al., *Applied and Environmental Microbiology,* vol. 57 (9), pp. 2724–2730 (1991).

Hartung and Civerolo, *Plant Disease,* vol. 75 (6), pp. 622–626 (1991).

Manulis et al., *Phytopathology,* vol. 81 (1), pp. 54–56 (1991).

Swarup et al., *Phytopathology,* vol. 81 (7), pp. 802–809 (1991).

Vauterin et al., *International Journal of Systematic Bacteriology.* vol. 41 (4), pp. a–h (1991).

Saiki et al., *Science,* vol. 239, pp. 487–491 (1988).

Hartung et al., *Applied and Environmental Microbiology,* pp. 1143–1148 (1993).

```
5'CGTTGCACCT CCCGCTGCAT GGGGTTGGTG TCGTCGCTTG TATGGCCTAT AGTCGATACT GGAAATCATT ATATATATAC ATAGATAAGT
3'GCAACGTGGA GGGCGACGTA CCCGCAACCAC AGCAGCGAAC ATACCGGATA TCAGCTATGA CCTTTAGTAA TATATATATG TATCTATTCA

ATATATATAC CTATCAACCC TTGAGGAAGG GCTTCCAGTG CCTCGATCAC GATGTCCTTC TCCGTGACCC TGCCGCCTTC TCTTCCGAGG
TATATATATG GATAGTTGGG AACTCCTTCC CGAAGGTCAC GGAGCTAGTG CTACAGGAAG AGGCACTGGG ACGGCGGAAG AGAAGGCTCC

CCTGAGGCCT GCGCGGGCAG GTGATCAGCC AGTTCCTCGG GGAAGTTGAA GATTTTTTGC ACCCGTGCGC GGCCGTAGCG CTGCGTTTCC
GGACTCCGGA CGCGCCCGTC CACTAGTCGG TCAAGGAGCC CCTTCAACTT CTAAAAAACG TGGGCACGCG CCGGCATCGC GACGCAAAGG
                                              1                                  2

TCAGCAGCGG GCGCGGTCGC TGCCGGTGTC GTGGTCACGG CAGCAGTGC TTCTCGGGCCT TGTCCGCCTC CGCCTTCGAG
AGTCGTCGCC CGCCGACCG ACGGCCACAG CACCAGTGCC GTCGTCCACG AAGAGCCGGA ACAGGCCGAG GCGGAAGCTC

GAAGCGTCGG TCTTGGCGGC TTGAACTGCG CCGTGTTGGG CTTGCCTTCA TGCTCATGCC ATCCACCTCC TTGAAGAAGG CTTCCATCTC
CTTCGCAGCC AGAACCGCCG AACTTGACGC GGCACAACCC GAACGGAAGT ACGAGTACGG TAGGTGGAGG AACTTCTTCC GAAGGTAGAG

GGCGATGGCG GCTTGATCGC GGCCCAACTC CTGAACGGTC GCACCCTCGC CAATGGGCGG GCGAAGGCC ACGGGCTCGC AGACCTTGGT
CCGCTACCGC CGAACTAGCG CCGGGTTGAG GACTTGCCAG CGTGGGAGCG GTTACCGCCC CGCCTTCCGG TGCGCAGCG TCTTGGAACCA
                                                         5                                        7

GGGCAGCACG GTCAGCTTCT GCCTCGGCCA AG 3'
CCCGTCGTGC CAGTCGAAGA CGGAGCCGGT TC 5'
```

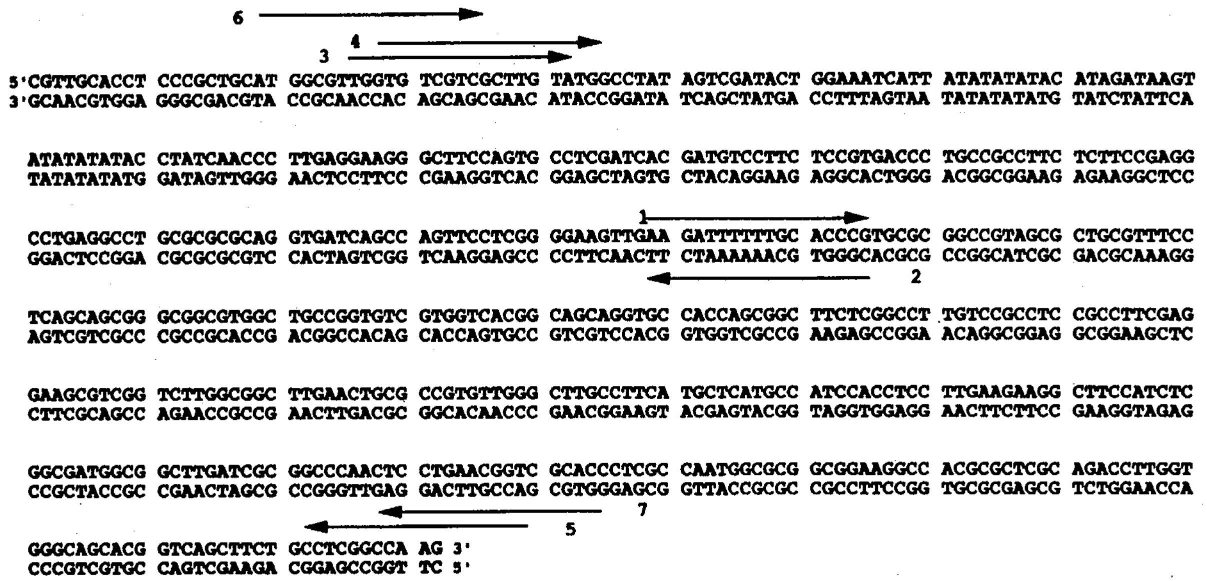

FIG. 5

SEQUENCE LISTING ( 1 ) GENERAL INFORMATION:

( i i i ) NUMBER OF SEQUENCES: 8

( 2 ) INFORMATION FOR SEQ ID NO:1:

-continued ( i ) SEQUENCE CHARACTERISTICS:
( A ) LENGTH: 572 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: YES ( i v ) ANTI-SENSE: NO ( v i ) ORIGINAL SOURCE:
( A ) ORGANISM: Xanthomonas campestris
( B ) STRAIN: Pathovar citri, strain XC62

( v i i ) IMMEDIATE SOURCE:
( B ) CLONE: pFL1

( x i ) SEQUENCE DESCRIPTION: SEQ ID NO:1:

CGTTGCACCT CCCGCTGCAT GGCGTTGGTG TCGTCGCTTG TATGGCCTAT AGTCGATACT 60

GGAAATCATT ATATATATAC ATAGATAAGT ATATATATAC CTATCAACCC TTGAGGAAGG 120

GCTTCCAGTG CCTCGATCAC GATGTCCTTC TCCGTGACCC TGCCGCCTTC TCTTCCGAGG 180

CCTGAGGCCT GCGCGCGCAG GTGATCAGCC AGTTCCTCGG GGAAGTTGAA GATTTTTTGC 240

ACCCGTGCGC GGCCGTAGCG CTGCGTTTCC TCAGCAGCGG GCGGCGTGGC TGCCGGTGTC 300

GTGGTCACGG CAGCAGGTGC CACCAGCGGC TTCTCGGCCT TGTCCGCCTC CGCCTTCGAG 360

GAAGCGTCGG TCTTGGCGGC TTGAACTGCG CCGTGTTGGG CTTGCCTTCA TGCTCATGCC 420

ATCCACCTCC TTGAAGAAGG CTTCCATCTC GGCGATGGCG GCTTGATCGC GGCCCAACTC 480

CTGAACGGTC GCACCCTCGC CAATGGCGCG GCGGAAGGCC ACGCGCTCGC AGACCTTGGT 540

GGGCAGCACG GTCAGCTTCT GCCTCGGCCA AG 572

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Xanthomonas campestris
( B ) STRAIN: Pathovar citri, strain XC62

( x i ) SEQUENCE DESCRIPTION: SEQ ID NO:2:

AGATTTTTTG CACCCGTG 18

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Xanthomonas campestris -continued ( B ) STRAIN: Pathovar citri, strain XC62

( x i ) SEQUENCE DESCRIPTION: SEQ ID NO:3:

CACGGGTGCA AAAAATCT 18

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Xanthomonas campestris
( B ) STRAIN: Pathovar citri. strain XC62

( x i ) SEQUENCE DESCRIPTION: SEQ ID NO:4:

TGGTGTCGTC GCTTGTAT 18

( 2 ) INFORMATION FOR SEQ ID NO:5:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Xanthomonas campestris
( B ) STRAIN: Pathovar citri, strain XC62

( x i ) SEQUENCE DESCRIPTION: SEQ ID NO:5:

TGTCGTCGCT TGTATGGC 18

( 2 ) INFORMATION FOR SEQ ID NO:6:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Xanthomonas campestris
( B ) STRAIN: Pathovar citri, strain XC62

( x i ) SEQUENCE DESCRIPTION: SEQ ID NO:6:

GACCGTTCAG GAGTTGGG 18

( 2 ) INFORMATION FOR SEQ ID NO:7:

( i ) SEQUENCE CHARACTERISTICS:
( A ) LENGTH: 18 base pairs
( B ) TYPE: nucleic acid
( C ) STRANDEDNESS: single -continued ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Xanthomonas campestris
( B ) STRAIN: Pathovar citri, strain XC62

( x i ) SEQUENCE DESCRIPTION: SEQ ID NO:7:

ATGGCGTTGG TGTCGTCG 18

( 2 ) INFORMATION FOR SEQ ID NO:8:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Xanthomonas campestris
( B ) STRAIN: Pathovar citri, strain XC62

( x i ) SEQUENCE DESCRIPTION: SEQ ID NO:8:

GGGTGCGACC GTTCAGGA 18

DETECTION OF *XANTHOMONAS CAMPESTRIS* PV. CITRI BY HYBRIDIZATION AND POLYMERASE CHAIN REACTION ASSAYS

This is a continuation-in-part of application Ser. No. 07/855,804, filed Mar. 23, 1992, now abandoned, herein incorporated by reference.

I. BACKGROUND OF THE INVENTION

1. Field of the Invention

Citrus bacterial canker disease (CBCD) is a serious disease of citrus, and the causal pathogen, *Xanthomonas campestris* pv. *citri* (Hasse) Dye (*X.c. citri*) is the subject of international quarantine. Although eradicated from the United States at great cost in the first third of this century, CBCD has reoccurred in several locations in Florida in recent years. A new eradication campaign has ensued, resulting in renewed interest in the disease and in methods for detecting the pathogen.

Several pathotypes within *X.c. citri* have long been recognized based on host range, geographical origin, bacteriophage sensitivities, plasmid content and serology. It is currently believed that at least three types of CBCD, types A, B and C, occur world-wide and are induced by variants of the same causal agent. These variants are primarily distinguished by their geographical origin and their host range. Pathotype A has both the widest host range and a global distribution. In addition, some pathogenic strains of *X. campestris* may also be associated with citrus bacteriosis in Mexico and have been described as the D type of the disease. Pathotypes B, C and D have so far been restricted to lemon (*Citrus limon*) and lime (*Citrus aurantifolia*) in South America and Mexico. The existence of the pathotypes has been confirmed at the DNA level by genomic fingerprinting (Hartung and Civerolo, 1987) and by restriction fragment length polymorphism (RFLP) analyses (Gabriel et al., 1988, and Hartung and Civerolo, 1989).

Another group of strains of *X. campestris*, which is genomically heterogeneous and different from *X.c. citri*, is associated with citrus bacterial spot disease (CBSD) in Florida. CBSD causes minor foliar damage primarily in citrus nurseries and is no longer considered a threat to the citrus industry. Strains of *X. campestris* that cause CBSD can be distinguished from strains of *X.c. citri* by the methods mentioned above as well as by symptomology (Schoulteis et al., 1987) and DNA/DNA hybridization (Egel et al., 1991).

Because of the magnitude of the perceived threat by *X.c. citri* to the citrus industry resulting in plant quarantines in both the United States and abroad, the development of diagnostic methodologies has been a high priority. Due to the occurrence of strains of *X. campestris* that cause CBSD on *Citrus* spp. and closely related plants, a high degree of specificity is now required.

This invention relates to diagnostic probes which are capable of detecting all four forms of CBCD and of distinguishing between the pathogens responsible for this disease and those causing CBSD. In addition, oligonucleotide primers useful for polymerase chain reaction (PCR)-based detection methods are also described. They may effectively be used by plant pathologists, microbiologists or regulatory agencies charged with the responsibility of detecting *X.c. citri* in interstate or international commerce.

DESCRIPTION OF THE PRIOR ART

*X.c. citri* is a heterogeneous pathogen, and several variants can be distinguished by serology, bacteriophage typing, analysis of genomic structure and virulence. The established techniques for identification of *X.c. citri* include bacteriophage sensitivity tests, pathogenicity tests, pigment analyses (Civerolo, 1984), enzyme-linked immunosorbent assays (Civerolo et al., 1982) and RFLP analyses (Hartung and Civerolo, 1989). All of these techniques require cultivation of the organism and require days or weeks to perform.

DNA-based methods have previously been developed for the identification of other phytopathogenic bacteria. A DNA-based method was developed for the detection of *Pseudomonas syringae* pv. *tomato* (P.s. tomato) (Denny, 1988). The probes used were chromosomally derived and cross reaction with the related bacterium *P.s. syringae* was described. A plasmid-based DNA probe was developed to identify *X.c. phaseoli* (Gilbertson et al., 1989). In contrast to the novel probes described herein, however, this probe contained a repeated sequence, and cross reactions with other pathovars were noted. A plasmid-based DNA probe was also developed to distinguish pathogenic from non-pathogenic strains of *Erwinia herbicola* (Manulis et al., 1991). Cross reactions with other strains were not reported, however, it was expected that cross reactions with other pathogens, particularly *P. savastanoi*, would occur. DNA-based probes were also demonstrated for the detection of *P.s. phaseolicola* (Schaad et al., 1989) and *Clavibacter michiganense* pv. *michiganense* (Thomson et al., 1989).

DNA probes derived from genomic DNA have been useful in RFLP studies of *X. campestris*. They are not useful as diagnostic probes, however, because the capacity to cross react with other pathovars of *X. campestris*, which is useful in RFLP studies, compromises their specificity.

II. SUMMARY OF THE INVENTION

DNA fingerprinting and RFLP analyses of plasmid DNA were used to distinguish the pathotypes of *X.c. citri* (i.e. types A, B, C and D). In the course of those studies, we discovered a fragment of plasmid DNA occurring only in *X.c. citri*. The fragment has been cloned and utilized to develop a sensitive diagnostic probe which specifically hybridizes to DNA from all pathotypes of *X.c. citri*. The DNA fragment did not hybridize with DNA isolated from other bacterial genera, or with DNA from most strains of *X. campestris* *which occur on other crops. In particular, the probe did not detect any strains which are the causal agent of CBSD. A small fragment was subcloned from the probe, thereby improving the specificity of the technique. The nucleotide sequence of the small fragment was determined, from which primers were designed for use with polymerase chain reaction methods, thereby enhancing detection capability.*

In accordance with this discovery, it is an object of the invention to provide novel probes effective for the diagnosis of CBCD, and particularly probes which specifically hybridize to plasmid DNA sequences of *X.c. citri*.

It is an additional object of the invention to provide novel oligonucleotide primers useful for amplification of target pathogen DNA.

It is also an object of the invention to provide plasmids effective for the production of the novel probes.

It is a further object of the invention to provide a sensitive, reliable and rapid hybridization assay method for the detection of *X.c. citri* for use in quarantine or diagnostic laboratories.

III. BRIEF DESCRIPTION OF THE DRAWINGS

FIG. 1A, B, C, D, E, F shows the chemiluminescent detection of *X.c. citri* with biotinylated hybridization probes in duplicate blots: the probe was pFL62.42 for blots A, B and C; the probe was pFL1 for blots D, E and F.

FIG. 2A, B shows the results of a dot blot hybridization assay for DNA from strains of *X.c. citri* and other bacterial genera, using the probe pFL62.42.

FIG. 3A, B shows a Southern blot of *X. campestris* genomic DNA after digestion with BamHI, using the probe pFL1.

FIG. 5 shows the DNA sequence of the 572-bp probe pFL1. Arrows indicate the relative positions and direction of priming of the primers used in this study.

Figure 7:
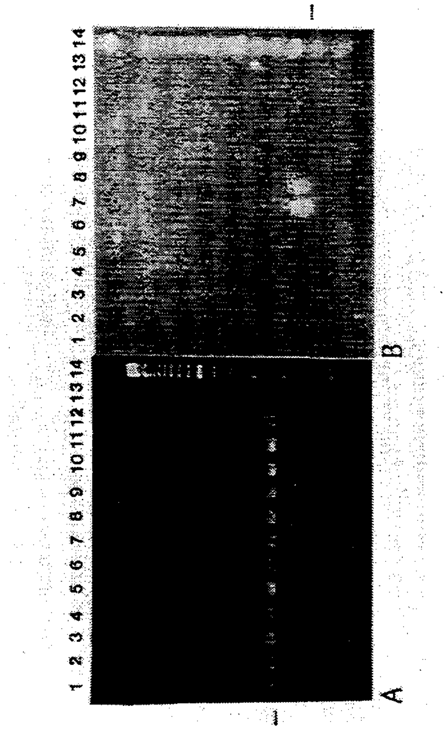

FIG. 7A, B shows specific amplification by PCR of target DNA from pathotype A strains of *X.c. citri* from 12 countries (A), pathotype B and C strains, *X. campestris* pvs. *alfalfae, bilvae* and *vignicola*, and CBSD strains (B).

FIG. 8A, B, C shows sensitivity of PCR technique using purified DNA (A) and cultured cells (B) as samples.

Figure 9:
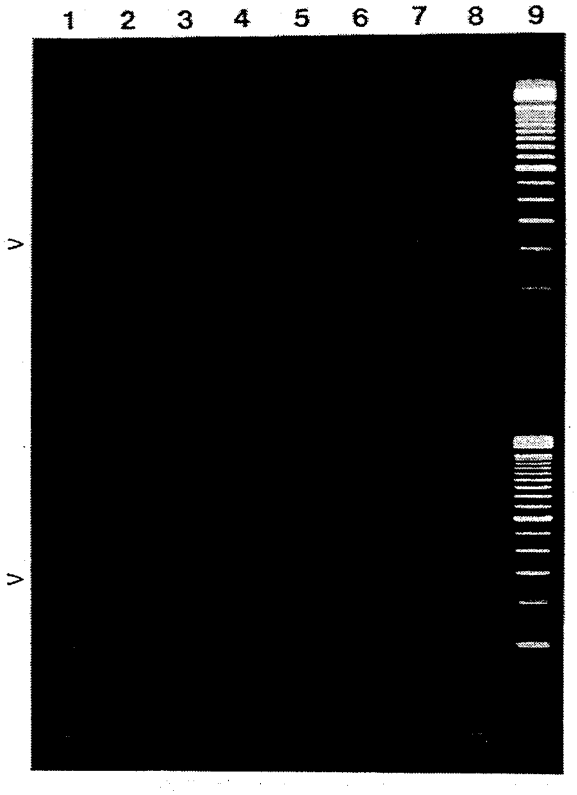

FIG. 9 shows the detection of DNA of strain XC320 by PCR after CTAB extraction of necrotic leaf lesions.

FIG. 10A, B shows the detection of DNA from strain XC320 in exudate from single cankers by gel electrophoresis (A) and a Southern blot of the gel (B)—after "cankers".

IV. DETAILED DESCRIPTION OF THE INVENTION

The novel probes of the invention were isolated as a result of work based on genomic DNA fingerprinting and RFLP analyses of *X. campestris* and *X.c. citri.* An approximately 4.2-kb BamHI fragment cloned from an indigenous plasmid of pathotype A strain XC62 and an approximately 572-bp internal EcoRI fragment derived from it were found to occur in all tested pathotype A strains and to have widespread occurrence in strains B, C and D. This conservation of particular plasmid DNA sequences within pathotype A, the most virulent and widespread pathotype, and the presence of related sequences in pathotypes B, C and D suggested that the sequences would make a useful probe for the specific identification of *X.c. citri*. Furthermore, since plasmids are generally present in multiple copies per cell, good sensitivity could also be expected. Thus the 4.2-kb BamHI fragment from a plasmid of strain XC62 and a 572-bp EcoRI fragment derived from it became attractive candidates for diagnostic probes.

The probes may be isolated, cloned and produced by methods well-known and conventional in the art, such as described by Maniatis et al. (1982).

Plasmid DNA may be extracted as described by Kado and Liu (1981). Extracted plasmid DNA from *X.c. citri* strain XC62 is digested with restriction endonuclease BamHI, and the fragments are separated by size. The 4.2-kb BamHI fragment may be further digested with restriction endonuclease EcoRI to produce the 572-bp fragment.

The fragments are cloned into the appropriate vector by conventional recombinant methods (e.g. Maniatis, supra). A preferred vector is pUC9; however, any effective standard vector may be utilized, and its selection is well within the level of skill in the art. The 4.2-kb BamHI fragment cloned in pUC9 is referred to as plasmid pFL62.42, and the 572-bp EcoRI fragment cloned in the same vector is referred to as plasmid pFL1.

Expansion of the probes may also be carried out by conventional methods (e.g. Maniatis, supra). For example, after ligation of the plasmid fragments into the vector, E. coli cells may be transformed with the ligation mixture by a known effective method such as a calcium chloride-mediated transformation. Following transformation, the cells are cultured under conditions which promote growth.

Probes are recovered from the cells by cell lysis and purification by such means as a cesium chloride/ethidium bromide gradient. The purified intact plasmid may then be utilized as probes. Alternatively, the probe insert may be released from the vector by digestion with the appropriate endonuclease (i.e. BamHI for pFL62.42 or EcoRI for pFL1), followed by fractionation and purification by such means as agarose gel electrophoresis.

To provide detection capability, the probes are suitably labeled by such labels as radioactive, enzymatic, fluorescent, luminescent or organic labels. Labeling procedures are dependant upon the label selected and are well known to the skilled artisan. Preferred labels are radioactive labels such as $^{32}p$ which may be visualized by autoradiography or organic labels such as biotin which are detectable by chemiluminescence. Particularly preferred is the biotin label for the obvious advantage of avoiding the hazards associated with the use of radioactive materials.

The novel probes of the invention are effective for use in hybridization assays such as the dot blot assay and Southern blot assay. Both assay methods utilize samples containing total bacterial genomic DNA and are carried out under high stringency conditions.

The samples may be obtained from leaf disks taken from canker lesions on citrus leaves. The disks are ground in liquid nitrogen, and the DNA extracted from leaf powder. Following extraction, the DNA samples are denatured and serially diluted for dot blot assay. The samples for Southern blot assay differ from dot blot assay preparations only in a digestion step using BamHI restriction endonuclease followed by preparative agarose gel electrophoresis following extraction from the leaf powder.

The ability of the probes to detect *X.c. citri* was evaluated in tests with a worldwide collection of strains (see Table 1). The specificity of the probes was evaluated in tests with a wide variety of strains of other pathovars of *X. campestris*, especially those strains associated with CBSD (Table 2), as well as bacteria from other genera (Table 3).

Probe pFL62.42 hybridized with DNA from all *X.c. citri* pathotype A strains from 13 countries (44/44), as well as 13/15 strains of pathotypes B, C and D from South America (FIG. 1A). Strong signals were obtained from strains XC98 and XC100 (FIG. 1A; C-6 and C-10, respectively) which had been shown previously to be distinguishable from other strains of *X.c. citri* by genomic fingerprinting and RFLP analyses. DNA from the pathotype B strain XC64 and pathotype C strain XC70 failed to hybridize with the probe. DNA from all other pathotype B, C and D strains

TABLE 1

Strains of *Xanthomonas campestris pv. citri* used in this study[a]

| Strain | Origin |
|---|---|
| Pathotype A[b] | |
| XC62, XC63 | Japan |
| XC101, XC102 | Guam |
| XC104, XC105 | Thursday Island |
| XC106, XC1O7 | Christmas Island |
| PH2, PH3, PH7 | Philippines |
| Th76, Th7B, Th7C | Thailand |
| XC74, XC75, XC77 | Reunion Islahd |
| MI1-1, MI2-2, MI3-1, MI4-7 | Maldive Islands |
| MI7-4, MI14-10, MI15-7, MI16-3, MI18-2 | |
| MIJJ97A | Mauritius |
| XC100, XC297, XC298 | Pakistan |
| XC269 | Saudi Arabia |
| XC98 | Yemen |
| XC118 | New Zealand (Type)[c] |
| XC91, XC92 | Argentina |
| XC336, XC337 | Uruguay |
| F598, F599, F600, XC308, XC312 XC320 | Florida, USA |
| Pathotype B | |
| XC64, XC69, XC93, XC94, XC96 XC148, XC80, XC84 | Argentina |
| Pathotype D | |
| XC90 | Mexico |
| Pathotype C | |
| XC70, XC171, XC172, XC338 XC340, XC341 | Brazil |

[a]All strains are from the collection of phytopathogenic bacteria of the Fruit Laboratory, Beltsville Agricultural Research Center, Beltsville, MD.
[b]Pathotypes as described in references 4 and 24.
[c]NCPPB409

TABLE 2

Additional bacterial strains used in this study[a]

| Strains | Comments[a] |
|---|---|
| *X. campestris* | |
| X60, X61 | pv. *alfalfae*; D.W. Gabriel |
| X3 | pv. *begoniae*; J.W. Miller |
| X32, X33 | pv. *bilvae*; IMI 8600, NCPBB[b] |
| X6, X7, X8 | pv. *campestris*; J.W. Miller |
| X11, X12 | pv. *dieffenbachiae*; J.W. Miller |
| X151 | pv. *fici*; J.H. Graham (14) |
| X56 | pv. *holcicola*; E.L. Civerolo |
| X22 | pv. *macufoliigardeniae*; J.W. MIller |
| X203 | pv. *malvacearum*; E.L. Civerolo |
| X40 | pv. *manihotis*; W. Fry |
| X18, X20 | pv. *nigromaculans*; J.W. Miller |
| X25 | pv. *pelargonii*; J.W. Miller |
| X34, X35, X36, X45 | pv. *phaseoli*; NCPPB, NCPPB, D.W. Gabriel ATCC |
| X69, X70 | pv. *pruni*; ICMP |
| X27, X37, X38 | pv. *vesicatoria*; J.W. Miller, R.E. Stall |
| X137, X143, X198 | from *Strelitzia reginae*; J.H. Graham (14) |
| G-55, 81-30, 82-38, 86-1 | pv. *vignicola*; R.E. Stall |
| T20, T22, T23, T24 | from *Citrus aurantifolia*; not pathogenic on *Citrus*; E.L. Civerolo |

[a]Pathovar or host of isolation, source and references.
[b]Abbreviations: ATCC — American Type Culture Collection, Rockville, MD; IMI — Indian Mycological Institute; NCPPB — National Collection of Plant Pathogenic Bacteria, Harpendon, England; ICMP — International Collection of Microbes from Plants, Auckland, New Zealand.

TABLE 3

| Other bacteria | |
|---|---|
| *Flavobacterium balustinum* 299 | D. Roberts |
| *Enterobacter cloacae* E6 | D. Roberts |
| *Escherichia coli* RR1 | (3) |
| *Erwinia carotovora* subsp. *carotovora* EC14 | D. Roberts |
| *Pseudomonas putida* 15819 | D. Roberts |
| *Erwinia amylovora* 11OR | (25) |

did hybridize with the probe, however, scanning laser densitometry of these blots using a dilution series of strain XC62 DNA as an internal standard showed that these (pathotypes B, C, D) signals were much weaker than the signals from pathotype A strains (FIG. 1A, row e; data not shown). In contrast to the strains of *X.c. citri*, the probe did not hybridize to any of the 56 CBSD strains tested, or to DNA from four epiphytic strains of *X. campestris* isolated from lime in Mexico (FIG. 1C). DNA from 16 other pathovars of *X. campestris* was also tested for sequences homologous to pFL62.42. Most strains did not have sequences homologous to pFL62.42. However, hybridization signals were detected from single strains of *X.c. alfalfae, X.c. bilvae, X.c. campestris* and from four tested strains of *X.c. vignicola*. Very faint signals, approximately equal in intensity to the signal produced by 1 ng of DNA from strain XC62 could be seen for DNA from several other pathovars (FIG. 1B). In contrast to the results from pathotypes B, C and D of *X.c. citri*, scanning laser densitometry showed that the signals from *X.c. bilvae* and *X.c. vignicola* were similar in intensity to those of pathotype A strains of *X.c. citri* (FIG. 1B, row e; data not shown).

Figure 1:
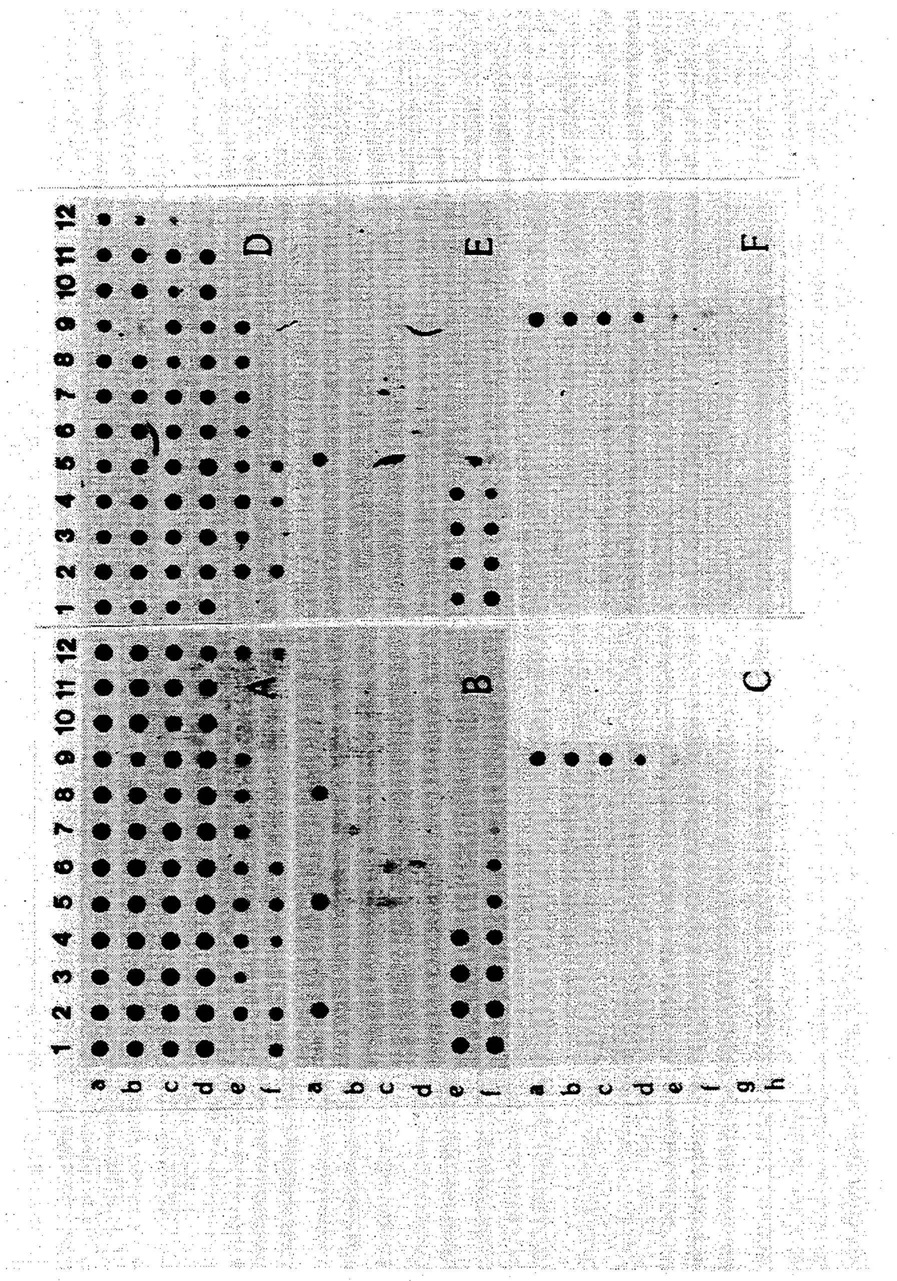

Duplicate filters processed in parallel with those in FIG. 1 A–C were probed with plasmid pFL1. Plasmid pFL1 retained the homology of pFL62.42 for *X.c. citri* (FIG. 1D), and also did not hybridize to DNA from CBSD strains of *X. campestris* (FIG. 1F). The specificity of pFL1 for *X.c. citri* compared to other pathovars of *X. campestris* was better than that of pFL62.42. Only *X.c. bilvae*, and *X.c. vignicola* produced significant hybridization signals with this probe (FIG. 1E). However, detection of pathotype C strains was somewhat less successful with pFL1 than with pFL62.42 (FIG. 1, A and D; row f).

No hybridization signal was detected with DNA isolated from strains belonging to other bacterial genera when the gel purified insert from pFL62.42 was used as a hybridization probe (FIG. 2A). However, DNA from *Escherichia coli* RR1 hybridized to vector sequences when intact pFL62.42 was used as the probe (FIG. 2B).

The sizes of the DNA fragments that hybridized to pFL1 were compared after BamHI digestion and Southern blotting. In the *X.c. citri* pathotype A strains tested, the homologous fragment was at 4.2-kb as expected (FIG. 3A). In contrast, the homologous fragment(s) in strains of heterologous pathovars were larger than 20-kb as was true for strains of *X.c. citri* pathotypes B, C and D (FIG. 3B). Analogous results were observed when pFL62.42 was used as the hybridization probe.

Figure 4:
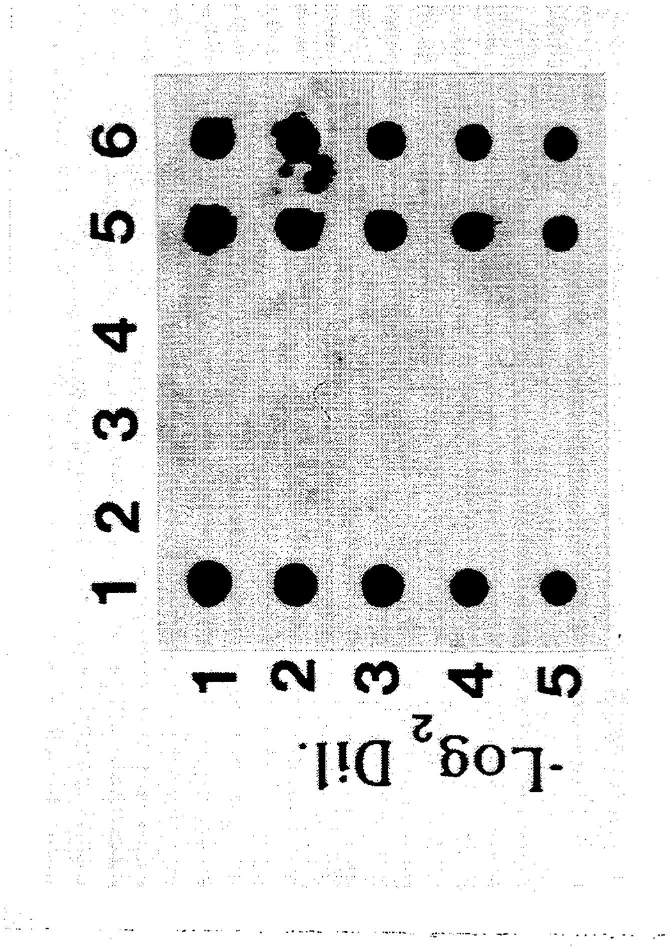
FIG. 4 shows the specific detection of pathotype A of *X.c. citri* in leaf lesions, using biotinylated probe pFL1.

Probe pFLI also detected homologous DNA sequences when present in leaf disks which contained CBCD-A lesions (FIG. 4). For both strains tested, pFL1 produced distinctly positive signals from each tested canker, even after the lesion extract had been diluted 1/32 or more. No signal was observed from the leaf disks taken from noninoculated control leaves or from leaf disks which contained CBSD lesions, even after prolonged exposure of the chemilumigrams. Another DNA isolation method, that combined the boiling "miniprep" procedure with glassmilk purification produced similar results with lesion extracts ground in liquid nitrogen as above (not shown).

The function (if any) encoded by pFL62.42 and pFL1 is unknown, although the conservation of the sequence within pathotype A strains, and the presence of related sequences in pathotype B, C and D strains of *X.c. citri* may suggest a role in host selection or some other biologically important function. It is significant that none of the strains of *X. campestris* which cause citrus bacterial spot disease had any sequences homologous to either pFL62.42 or pFL1. This is consistent with their limited relatedness to *X.c. citri*, and with their possible incidental association with citrus. The presence of homologous sequences in the single available strain of *X.c. bilvae* is interesting because the strain was originally isolated from *Feronia elephantiacum*, a member of the *Rutaceae*.

Figure 3:
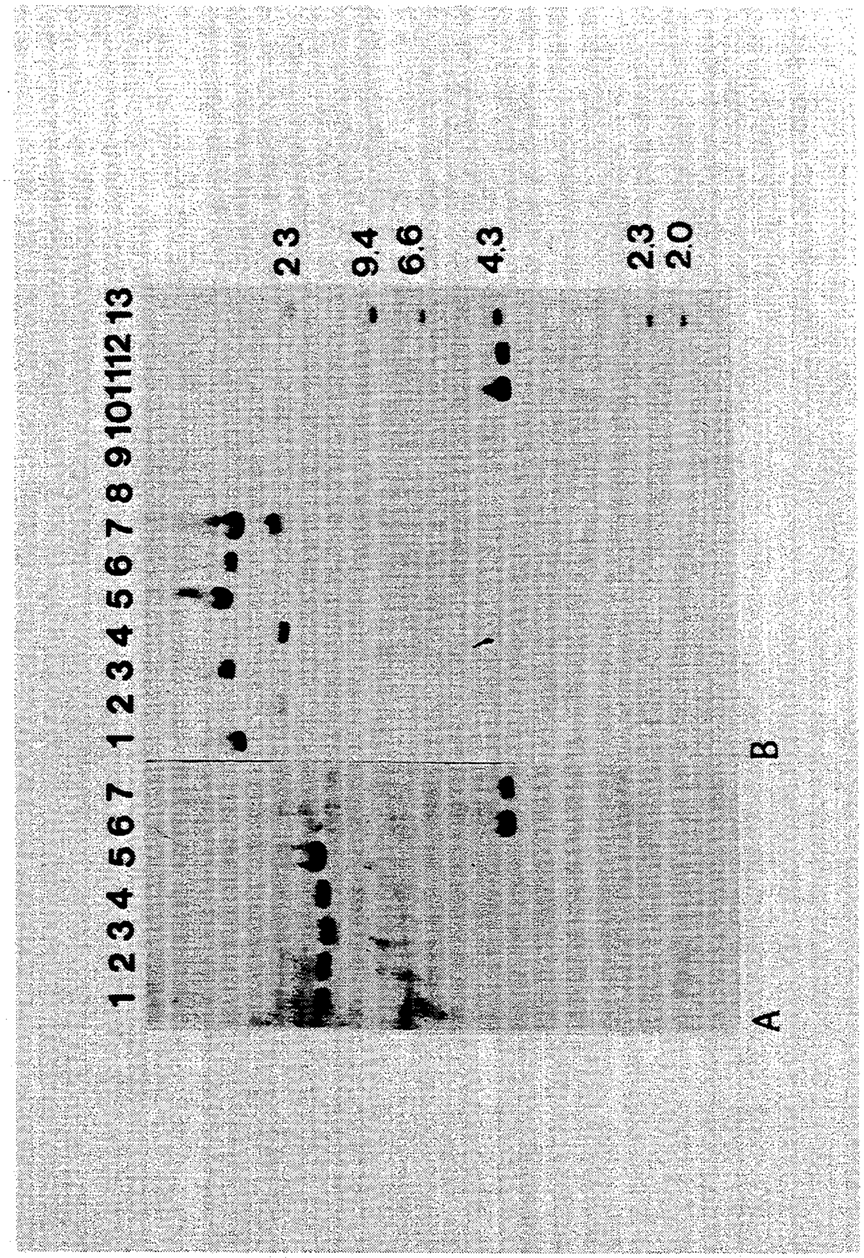

A pathogenicity locus which included a gene designated pthA was isolated recently from a genomic library of a pathotype A strain of *X.c. citri* (Swarup et al., 1991). pthA was included on a 3.7 kb SstI-Sal1 fragment, and no hybridization signal was observed in the region of 4.2 kb in BamHI digests of genomic DNA of *X.c. citri*. When pFL62.42 and pFL1 were used to probe similar digests, a band at 4.2 Kb was observed (FIG. 3). Thus, the hybridization probes described in this paper are unrelated to pthA.

The ability of these probes to hybridize to homologous sequences present in lesion extracts make them particularly valuable as diagnostic tools. However, DNA isolation was required for this purpose. Spurious hybridization signals were detected from F1 and F100 lesions (CBSD) when leaf squashes or similar unpurified extracts were probed (not shown).

The probes described herein provided excellent specificity within *X. campestris* for strains of *X.c. citri*, especially those belonging to pathotype A, the most widespread and virulent pathotype. The sensitivity of detection was in the range of 2–7 ng DNA/dot (FIG. 1), or the amount of DNA present in a single canker lesion (FIG. 4). Interference from other xanthomonads associated with *Citrus* was not observed. The demonstrated effectiveness of these probes with a non-radioactive label and the effect of quarantine regulations directed against *X.c. citri* on commerce make these probes particularly useful in regulatory situations, complementing current serological, phage typing and pathological methods.

In an alternative embodiment, the use of polymerase chain reaction (PCR) technology is contemplated. Such technology is applied to amplify sequences homologous to the probe, thereby increasing sensitivity substantially. Oligonucleotide primers synthesized according to the sequence of the probe direct DNA amplification only if the target sequence is present in the sample. In addition to increased sensitivity, the use of unique oligonucleotide primers based on the sequence of the DNA probe also results in absolute specificity.

In order to design effective primers, the nucleotide sequence of pFLI was determined (FIG. 5 SEQ ID NO:1). The Eco RI insert from pFLI was cloned into the sequencing vectors M13mp18 and M13mp19, and the DNA sequence was determined by conventional methods (Maniatis, supra). The sequence information was then used to design seven primers 18 bp in length using the computer program Nuc-it (Compu-Right, Gaithersburg, Md.). The primers were tested with DNA from *X.c. citri*, and paired primers were selected having low homology to other sequences in the target DNA fragment and having closely matched calculated thermal melting points. (Hartung et al., 1993, herein incorporated by reference.) The nucleotide sequence of each primer is presented in Table 4.

The novel primers are effective for use in PCR assays which have been previously described and are known in the art [Saiki et al., 1988 or Mullis (U.S. Pat. No. 4,683,202) 1987]. Essentially, the primers are used to amplify target DNA contained within a sample to achieve a level of DNA which is sufficient to render it detectable. Following the amplification step, a detection step is carried out by any means which is effective for detecting DNA. The preferred methods are Southern blot and dot blot hybridization assay methods.

TABLE 4

| Primer | Sequence |
|---|---|
| 1 | 5'AGA TTT TTT GCA CCC GTG 3' |
| 2 | 5'CAC GGG TGC AAA AAA TCT 3' |
| 3 | 5'TGG TGT CGT CGC TTG TAT 3' |
| 4 | 5'TGT CGT CGT TTG TAT GGC 3' |
| 5 | 5'GAC CGT TCA GGA GTT GGG 3' |
| 6 | 5'ATG GCG TTG GTG TCG TCG 3' |
| 7 | 5'GGG TGC GAC CGT TCA GGA 3' |

The target DNA serves as a template, and amplification of the template DNA of the sample is carried out by primer pairs which are used to treat the double-stranded DNA. The treatment results in extension products which are complementary to each nucleic acid strand. Each extension product synthesized can then serve as a template for the other primer. The treatment process includes denaturing the DNA, annealing the primers to their complementary sequences and extending the primers with DNA polymerase (i.e. Taq polymerase), and it is repeated a sufficient number of times to produce a detectable quantity of DNA which is indicative of the presence of the analyte in question.

Following amplification, the amplified sequences may be detected by the methods described herein, i.e. by dot blot or Southern blot assay procedures utilizing the novel probes pFL 42.62 or pFL1.

Primer pairs ¾ (SEQ ID NO:3/SEQ ID NO:4), 4/5 (SEQ ID NO:5/SEQ ID NO:6), 6/7 (SEQ ID NO:7-/SEQ ID NO:8) and 1/5 (SEQ ID NO:2/SEQ ID NO:6) were expected to prime amplification products of 222 bp, 462 bp, 478 bp and 261 bp, respectively, when utilizing the 572 bp DNA sequence as a target fragment. The DNA sequence of that fragment was 60.6% G+C. Because of the high G+C content and the fact that the target sequence was part of a plasmid, difficulty in achieving amplification was anticipated. Since buffer compositions can affect PCR results, three buffer compositions were tested for effectiveness (see Table 5 for buffer compositions).

| | |
|---|---|
| Buffer I: | 10 mM Tris/ce (pH 8.3) |
| | 50 mM Kcl |
| | 3 mM $Mg^{2+}$ |
| Buffer II: | 10 mM Tris/cl (pH 8.3) |
| | 50 mm Kcl |
| | 3 mM $Mg^{2+}$ |
| | 3% formamide |
| | 7% glycerol |
| Buffer III: | 50 mM Tris/Hcl (pH 9.0) |
| | 20 mM NaCl |

-continued

| |
|---|
| 1% Triton x-100 |
| 0.1% gelatin |
| 3 mM $Mg^{2+}$ |

Buffer I was the standard PCR buffer (recommended by Perkin Elmer/Cetus); buffer II was the standard buffer (buffer I) supplemented with glycerol and formamide; and buffer III differed from the standard buffer by having a higher pH and by incorporating 1% Triton x-100 and 0.1% gelatin. No amplification of homologous target DNA was achieved using buffers I and II at any annealing temperature from 45° C.–65° C. The only exception was primer pair 1/5 (SEQ ID NO:2/SEQ ID NO:6) which successfully primed amplification of its target sequence when annealed at 65° C. In contrast, specific amplification products were produced in buffer III at all temperatures from 45° C. to 65° C. with all four primer pairs. The results from the 55° C. annealing reaction are typical and are shown in FIG. 6A. Non-specific products were eliminated when the annealing temperature was 60° C. (FIG. 6B).

Specific amplification of target sequences in genomic DNA from 12 CBC-pathotype A strains which were originally isolated in 12 countries was carried out using primer pair 2/3 (SEQ ID NO:3/SEQ ID NO:4) (FIG. 7A). The primer pair did not detect target sequences in DNA from five strains of pathotypes B, C and D (FIG. 7B, lanes 1–5), however, or in DNA from four strains of *X. campestris* associated with CBSD (lanes 9–12). A product was found when DNA from single strains of *X.c. pvs. vignicola* and *bilvae* were tested (lanes 6–8).

The other primer pairs detected all 12 pathotype A strains tested, but gave variable results with strains representing pathotypes B, C and D. As with primer pair 2/3 (SEQ ID NO:3/SEQ ID NO:4), products were detected when DNA from *X.c. vignicola* and *X.c. bilvae* were tested.

The results of these pCR assays are consistent with hybridization analysis of these same strains. Pathotypes B and C strains have given consistently weaker results than pathotype A strains in dot blot assays and produced homologous bands of different sizes in Southern blots. The DNA from other bacterial species and from other pathovars of *X. campestris* was not detected in dot blot assays using pFLI as probe except for *X.c. vignicola* and *X.c. bilvae*, as with the PCR results. These strains are not known to occur on citrus and are unlikely to cause problems in the practicial application of these methods. In addition, pathotypes B and C are less virulent than pathotype A of *X.c. citri*, and are much less widely distributed, therefore posing less of a threat to the citrus industry.

Significantly, none of the primer pairs found targets in CBSD strains tested (FIG. 7B), consistent with dot blot assays using pFLI as probe of 54 CBSD strains. The specificity of detection demonstrated by pFLI in the dot blot experiments was therefore retained by the PCR assay. The clear detection of pathotype A and non-detection of pathotypes B and C in conjunction with the non-detection of CBSD strains present a useful complement to serological and dot blot procedures.

To evaluate the sensitivity of the PCR assay, a dilution series of genomic DNA from strain XC62 was prepared, and aliquots were used as templates for PCR amplification. Aliquots containing only 50 pg of genomic DNA were successfully detected after amplification with primer pair 1/5 (SEQ ID NO:2/SEQ ID NO:6) and Southern blotting (FIG. 8A). A dilution series of cultured cells of strain XC63 gave a limit of detection of about 10 cfu/reaction after amplification with primer pair 2/3 (SEQ ID NO:3/SEQ ID NO:4) and Southern blotting (FIG. 8B).

Thus the PCR method allowed the detection of 10 cfu/10 μl or the equivalent of $1 \times 10^3$ cfu/ml. Although this is not the detection of a single cell theoretically possible using PCR, the sensitivity is equivalent or better than generally obtained with serological techniques such as ELISA or immunofluorescence using polyclonal or monoclonal antibodies. Detection based on plating or semi-selective agar media also has the potential to detect single viable cells, but is very laborious and slow. In addition, specific amplification of target DNA was successful when starting with intact bacteria (FIG. 4B). In the dot blot assay method using probe pFL1, specific detection required purified DNA and was not possible with lysed bacteria due to the production of non-specific signal with the strepavidin-alkaline phosphatase conjugated reagent used for chemiluminiscent detection. The specificity of the reaction products was confirmed in all cases by the absence of product in the negative controls, the predicted product size and by Southern blotting. Thus the PCR assay represents an increase in speed and flexibility as well as an increase in sensitivity of at least 100-fold over the dot blot method of delection.

While amplification was successful with genomic DNA of pathotype A of *X.c. citri*, yield was improved if the DNA was digested with BamHI or EcoRI before amplification. This is probably due to the supercoiled (plasmid) state of the target DNA which would allow it to renature more quickly after heat denaturation than would linear DNA.

Figure 8:
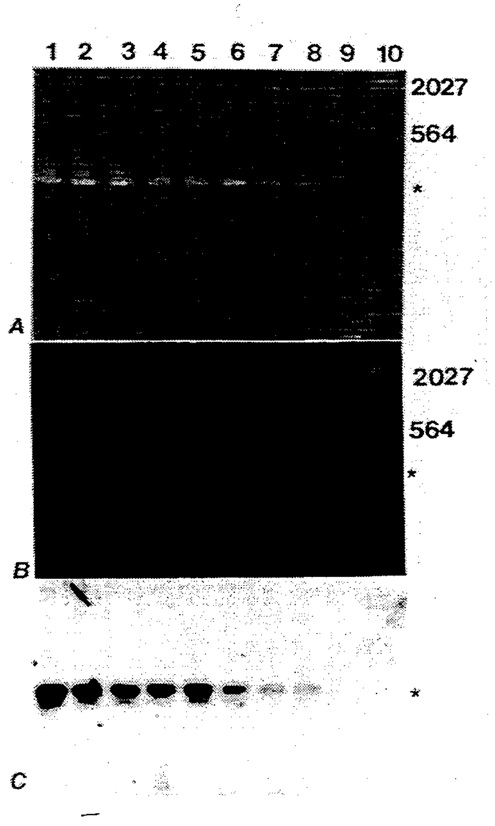

In an attempt to increase the sensitivity of the PCR assay, 5-μl aliquots of the experiments shown in FIG. 8 were subjected to a second round of PCR using conditions identical to the first round of amplification. This did not result in enhanced production of specific product.

Figure 10:
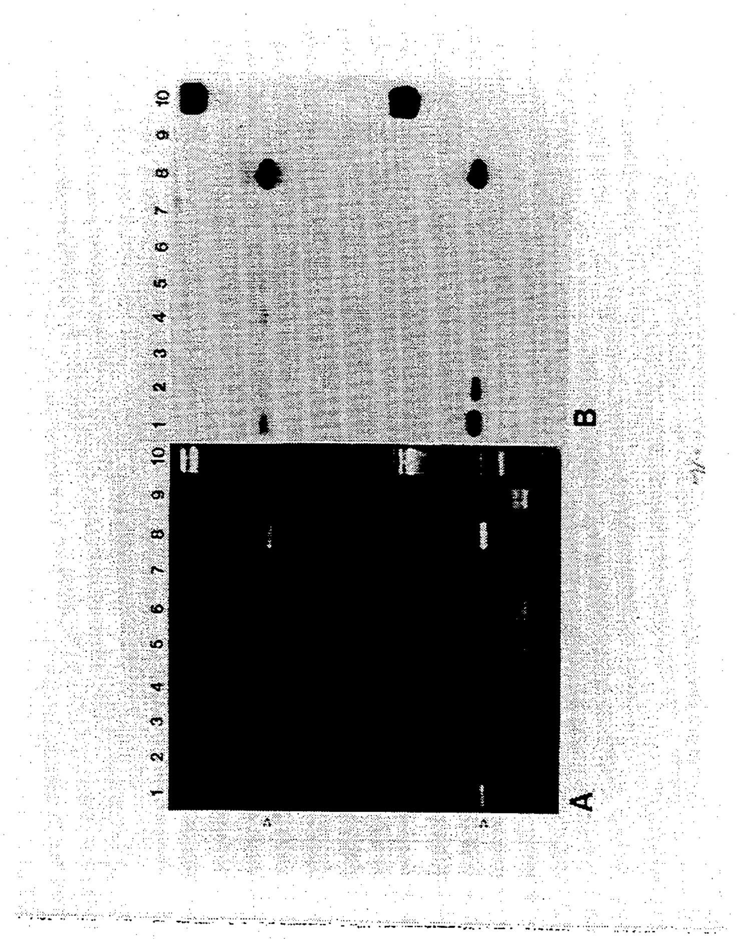

Specific amplification of target DNA obtained from lesion extracts was carried out, and the increase in sensitivity was similar. The specific detection of *X.c. citri* pathotype A DNA was achieved in dry necrotic lesions from which viable bacteria were not recovered (FIG. 9 and FIG. 10). Immature leaves of greenhouse grown grapefruit were inoculated with *X.c. citri* strain XC 320. After seven months, the lesions were old and dry. A sample containing purified DNA was prepared by removing two lesions with a paper punch, grinding together in liquid nitrogen and extracting the DNA with a CTAB (hexadecyltrimethylammonium bromide) protocol. A second sample used a crude water extract as a source for template DNA and was prepared by removing lesions with a paper punch and mincing with a razor blade in distilled water. Specific amplification of target DNA was observed after CTAB extraction of seven-month-old dry lesions incited by strain XC 320 in 4 of 4 assays utiizing primer pairs 1/5 (SEQ ID NO:2/SEQ ID NO:6), and 2/3 (SEQ ID NO:3/SEQ ID NO:4), (FIG. 9). Water extracts from the same set of lesions also produced specific amplification products (FIG. 10A). These products were detectable even when the extract was diluted 100-fold prior to amplification if the amplification products were subjected to Southern blotting and hybridization with probe pFL1 (FIG. 10B). No products were observed from healthy non-inoculated leaf disks assayed as controls. No viable bacteria were recovered from the necrotic lesions used in these assays.

The assay was repeated using succulent three-week-old lesions incited by strain XC63 with similar results, except that specific detection in triplicate assays was achieved after 100-fold dilution, corresponding to 100–800 cfu/assay. Viable bacteria were recovered from these lesions. It should be noted that populations of $10^6$ cfu/lesion have been reported in nine-month-old CBCD lesions on grapefruit (Stall et al., 1980, *Proc. Fla. Stat. Hort. Soc.*, 93:10–14). The absence of viable bacteria in the seven-month-old dry lesions is probably due to the frequent high temperatures occurring in the greenhouse during this period.

The PCR assay is a useful addition to previous detection methods because of the demonstrated combination of speed, sensitivity and specificity, all of which are critical to any assay for the detection of bacteria.

The following examples are intended only to further illustrate the invention and are not intended to limit the scope of the invention as defined by the claims.

All references cited herein are herein incorporated by reference.

EXAMPLE 1

Isolation of Plasmid DNA

Cultures of *X.c. citri* strain XC64 were grown for 24 hours at 28° C. on LPA medium containing 7 g yeast extract, 7 g bactopeptone, 15 g agar, 1000 ml distilled water at pH 7.2. The cultures were then transferred to flasks containing 20 ml of modified Wilbrink's broth (5 g bactopeptone, 2.5 g sucrose, 0.5 g $K_2HPO_4$, 0.25 g $MgSO_4$, 1000 ml distilled water) and shaken for 18 hours at 28° C. The cultured cells were collected by centrifugation using a Beckman JA 20 rotor at 10,000 rpm for 15 min at 4° C. The pellets were resuspended in 2 ml sterile TE buffer (10 mM Tris, 1 mM EDTA, pH 8.0). Cells were lysed using 4 ml lysing solution (3% SDS, 50 mM Tris, adjusted to pH 12.6 with NaOH) as described by the Kado and Liu, 1981, supra. Samples were incubated for 15 min at room temperature, then for 2 hrs at 65° C., the time required to completely degrade the genomic DNA. Samples were extracted with phenol-chloroform-isoamyl alcohol (24-24-1) and centrifuged as described above. One ml of sodium acetate (3M, pH 5.2) was added to 5 ml of the aqueous phase containing the plasmid DNA. Samples were incubated on ice for 10 min, then centrifuged as described above. Plasmid DNA was precipitated by adding two volumes of cold 95% ethanol and incubating for 1 hr at −20° C. DNA obtained after centrifugation at 13,000 rpm for 15 min at 4° C. was washed with 5 ml 70% ethanol. Pellets obtained after centrifugation were resuspended in 500 μl TAE buffer (Kado and Liu, 1981, supra) and stored at 4° C.

EXAMPLE 2

Preparation of pFL62.42 and pFL1 Probes

Extracted DNA was digested with restriction endonuclease BamHI according to manufacturer's specification (GIBCO/BRL) resulting in the 4.2-kb double-stranded plasmid DNA fragment utilized for pFL62.42. The 4.2-kb BamHI fragment was further digested with restriction endonuclease EcoRI to produce the 572-bp fragment used for pFL1. Plasmid and plasmid fragments were separated by size using agarose gel electrophoresis (SEAKEM LE agarose obtained from Marine Colloids, Rockland, Me.) at 5 V/cm in TAE buffer (pH 8.0), and the desired fragments were eluted with glass-milk (obtained from Bio101). Following elution, the fragments were ligated into vector pUC9 to form their respective recombinant DNA vector plasmids pFL62.42 and pFL1. These vector plasmids were subsequently used to transform E. coli cells for expansion of the probes.

EXAMPLE 3

DNA Test Sample Preparation

Test samples of genomic DNA were prepared as described by Hartung and Civerolo, 1987, supra. Bacterial cultures were centrifuged for 10 min at 10,000×g, and the resulting pellets were resuspended in 10 ml PBS (20 mM potassium phosphate buffer, pH 6.9, containing 150 mM NaCl). After a second centrifugation, the pellets were resuspended in 5 ml of 50 mM Tris, pH 8.0, containing 5 mM EDTA. Eggwhite lysozyme was added to a final concentration of 1 mg/ml, and the tubes were incubated at 0° C. for 30 min. One ml of freshly prepared lysing solution (0.5% SDS, 50 mM Tris/Cl, pH 7.5, 400 mM EDTA, and 1 mg/ml of pronase) was added to each tube, which was incubated at 50° C. until the suspension cleared. The lysate was extracted with an equal volume of Tris buffer-saturated phenol (pH 7.8). After centrifugation at 9000×g for 10 min, the aqueous supernatant was transferred to a clean tube and sodium acetate was added to 0.3M. After addition of two volumes of ethanol and mixing by inversion, the nucleic acids were removed by spooling onto a glass pipette and dissolved in 3 ml of TE (10 mM Tris/Cl, pH 8.0, 1 mM EDTA) containing RNase A (50 μg/ml). After 30 min at 37° C., the solution was extracted with an equal volume of chloroform, and the DNA was spooled out of the solution by a second ethanol precipitation. The DNA was dissolved in a minimal volume of TE and stored at 4° C. until used. Concentrations of DNA in the test samples may be determined spectrophotometrically.

EXAMPLE 4

Dot Blot Hybridization Assay

Fifty-nine strains of *X.c. citri* were isolated from diseased *Citrus* in 15 countries (Table 1). Thirty-eight strains representing 17 pathovars of *X. campestris*, four non-pathogenic strains of *X. campestris* (Table 2) and six strains from other bacterial genera (Table 3) were also tested. Fifty-six of these strains from 18 locations were tested for sequences homologous to pFL62.42 and pFL1. Total genomic DNA was extracted from the bacterial cultures as described in Example 3 (plasmid DNA was not precipitated out of the mixture), and the samples were pipetted into 96-well microtiter plates for denaturing and dilution. Denaturing was achieved using an equal volume of 0.4N NaOH at 25° C. for 10 min, followed by dilution with nine volumes of ice cold 1.1M ammonium acetate. Dot blots were prepared using a Hybri-Dot manifold and nylon Photogene filter membranes (GIBCO/BRL). Each dot contained 125 ng DNA/dot. Filters were baked for 90 min at 80° C. to fix the DNA.

Hybridization probes were prepared by releasing the plasmid vectors from the transformed E. coli cells by cell lysis followed by purification with cesium chloride/ethidium bromide density gradients. Purified double-stranded plasmid DNA probe was the labeled with biotin by nick translation using the Bio-Nick kit (GIBCO/BRL) with biotinylated dATP.

Figure 2:
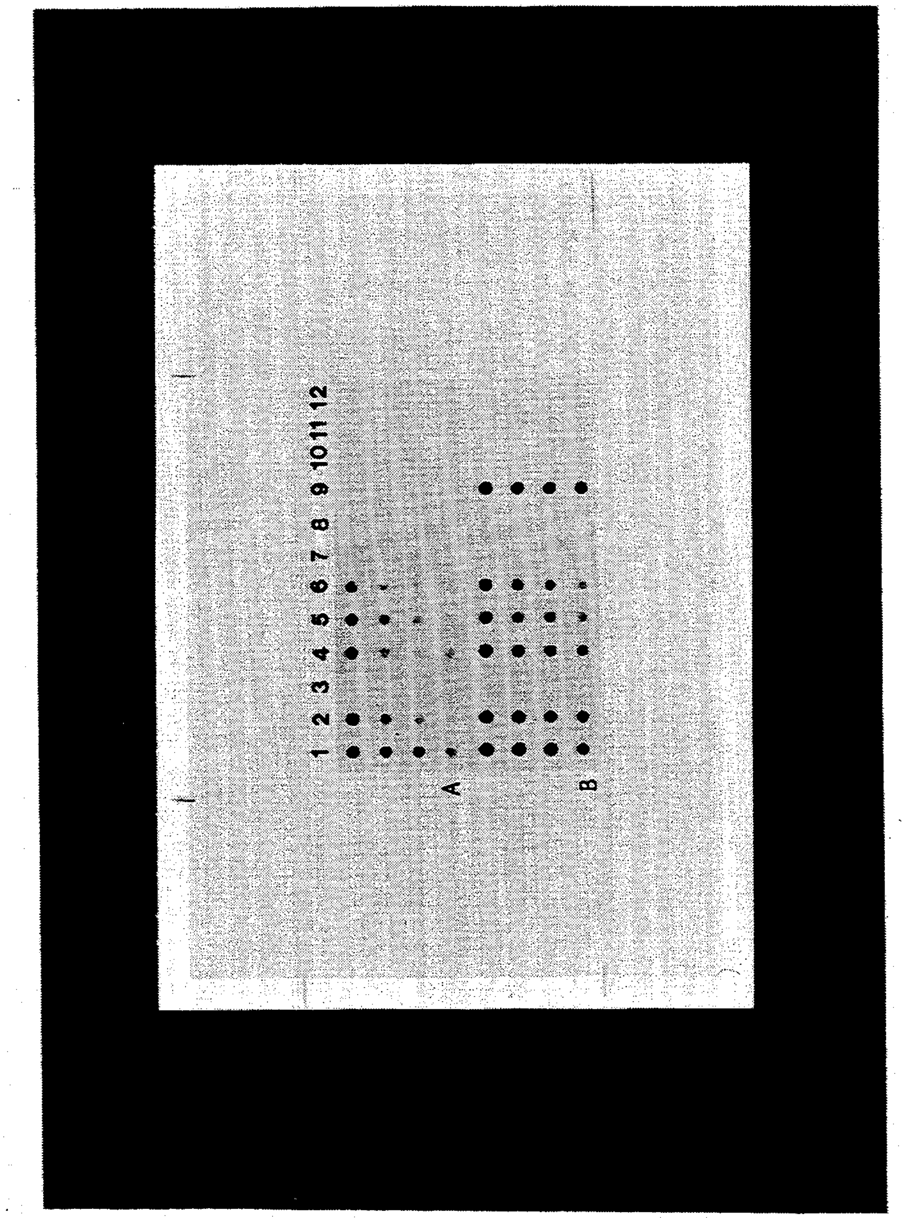

Hybridizations were done under high stringency conditions in a 10-ml volume in roller bottles with a hybridization oven (Techne HB-1, Thomas Scientific) at 68° C. for 18 hr using a standard hybridization solution (6 X SSC, 0.01M EDTA, 5 X Denhardt's solution, 0.5% SDS and 100 μg/ml denatured salmon sperm DNA) and 400 ng probe/filter. After hybridization, the filters were washed twice in roller bottles at 68° C. with 50 ml 0.1 X SSC, 0.5% SDS for each filter and three times with TBS-Tween (0.1M Tris, 0.15M NaCl, 0.05% Tween, pH 7.5). Detection was achieved using the Photogene chemiluminescent kit (GIBCO/BRL) following the directions of the manufacturer. After addition of chemiluminescent substrate, the filters were incubated in the dark for 150 min. Hyperfilm (Amersham) was exposed for 2–10 min. Results are shown in FIGS. 1 and 2, where for FIG. 1 blots A and D are 44 pathotype A strains of *X.c. citri* in rows a–d, columns 1–11, as listed in Table 1, row e contained DNA from the 9 pathotype B and D strains as listed in Table 1, row f contained DNA from the 6 pathotype C strains as listed in Table 1, Column 12 contained a 2-fold dilution series of XC62 (homologous) DNA beginning with 125 ng in dot a-12; blots B and E are DNA from 34 strains representing 16 pathovars of *X. campestris* as listed in Table 2, in rows a-c columns 1–8, row d columns 1–6, and row e columns 1–4, row f contained a 2-fold dilution series of XC62 DNA, beginning with 125 ng in dot f-1; blots C and F are DNA from 56 strains of *X. campestris* associated with citrus bacterial spot disease in rows a–g, columns 1–8, row h columns 1–4 contained DNA from epiphytic strains of *X. campestris* isolated in Mexico, and column 9 contained a 2-fold dilution series of XC62 DNA, beginning with 125 ng in dot a-9; and for FIG. 2, in duplicate blots, for blot A, the probe was the 4.2-kb BamHI fragment from pFL62.42; for blot B, the probe was pFL62.42, and DNA from strains XC62, XC69, XC70, and XC90 (*X.c. citri*), *X.c. bilvae* X33, *X.c. vignicola* 86-1, *Flavobacter balustinum* 299, *Enterobacter cloacae* E6, E. coli RR1, *Erwinia carorovora subsp. carocovora* EC14, *Pseudomonas putida* 15819, and *Erwinia amylovora* 110R were in rows 1–12.

EXAMPLE 5

Southern Blot Hybridization Assay

For Southern blotting, genomic DNA was extracted from *X. campestris*, as described in Example 3, and digested with endonuclease BamHI (4 U/μg) for 3 hrs at 37° C. Aliquots of 500 ng were electrophoresed at 20 V for 16.5 hrs in 0.8% agarose in TAE buffer. Capillary transfers were made to Photogene filter membranes (GIBCO/BRL) and were fixed by baking at 80° C. for 90 min. Hybridizations were performed using pFL1 as probe at 400 ng probe/filter. Hybridization and detection steps were as described in Example 4. Results are shown in FIG. 3, where Blot A: *X.c. vignicola* strains G55, 81–30, 82–38, 86–1 in lanes 1–4; *X.c. bilvae* strain X33 in lane 5; *X.c. citri* strains XC62 and XC100 (pathotype A) in lanes 6 and 7. Blot B: *X.c. citri* strains XC69, XC93, XC94, XC96, XC80, XC84, XC90 (pathotypes B and D) in lanes 1–7; strains XC70, XC171, XC172 (pathotype C) in lanes 8–10; strains XC62 and XC100 (pathotype A) in lanes 11 and 12. Sizes of biotinylated lambda/HindIII markers (lane 13) are shown in the margin.

EXAMPLE 6

Detection of Bacteria in Citrus Canker Lesions by Dot Blot Hybridization Assay Strains XC312, XC320 (*X.c. citri*) CBCD - Pathotype A), F1 and F100 (*X. campestris* CBSD) were grown from single colonies overnight in LPG medium (7 g tryptone, 7 g yeast extract, 7 g glucose, pH 7.2) and adjusted to an $OD_{590}$ of 0.1 with fresh LPG. Droplets (10 μl) were placed on the upper surfaces of newly expanded grapefruit leaves and a 25 gauge needle was used to wound the leaf through the inoculum. After 42 days, lesions were removed as 6 mm disks with a paper punch. Disks from uninoculated leaves served as controls.

Four leaf disks per strain were ground in liquid nitrogen. The leaf powder was taken up in CTAB buffer (50 mM Tris-HCl, pH 8.6, 7M NaCl, 10 mM EDTA, 1% CTAB, 2% Sarkosyl, and 0.1% mercaptoethanol), incubated at 60° C. for 5 hrs, extracted sequentially with phenol and chloroform and then ethanol precipitated. The DNA was resuspended in 25 μl TE buffer and diluted serially for dot blot assays, performed as described in Example 4 and using probe pFL1. Results are shown in FIG. 4, where column 1 contains purified DNA from strain XC62 (positive control) beginning with 125 ng; column 2 contains DNA from control inoculation sites (negative control); columns 3–4 contain DNA purified from lesions incited by CBSD strains F1 and F100, respectively; columns 5–6 contain DNA purified from lesions incited by CBCD A strains XC312 and XC320, respectively.

EXAMPLE 7

PCR Assay Method

PCR assays were performed in a DNA Thermal Cycler (Perkin Elmer/Cetus). Reaction volumes of 50 μl typically contained 50 ng genomic DNA, dNTPs at 200 μM and primers at 1 μM each in reaction buffer III (Table 5). Denaturation was carried out at 95° C. for 70 seconds; annealing at 58° C. for 60 sec and extension at 72° C. for 1 min plus an additional 2 sec/cycle, for 2 cycles. This program was linked to a second program of 33 cycles with a denaturation time of 30 sec. The other parameters were unchanged.

After amplification, detection is carried out by gel electrophoresis, Southern blotting and/or dot blot hybridization. Aliquots containing 25% of the reaction were removed and subjected to agarose gel electrophoresis [3 parts Nusieve: 1 part standard LE agarose (FMC, Rockland, Me.)] or 1.5% LE agarose gels. Southern blotting, DNA labeling and hybridization, and chemiluminescent detection was carried out as described in Examples 3 and 4.

The oligonucleotide primers were commercially synthesized by request (Genosys, The Woodlands, TX).

EXAMPLE 8

Evaluation of Reaction Buffers for Amplification of Target DNA

Three reaction buffers were tested (see Table 5 for buffer compositions). Amplification was carried out as described in Example 7, with the exception that two annealing temperatures—55° C. and 60° C. —were utilized. The template DNA was 50 ng of EcoRI digested pathotype A DNA from strain XC62 for all reactions.

Figure 6:
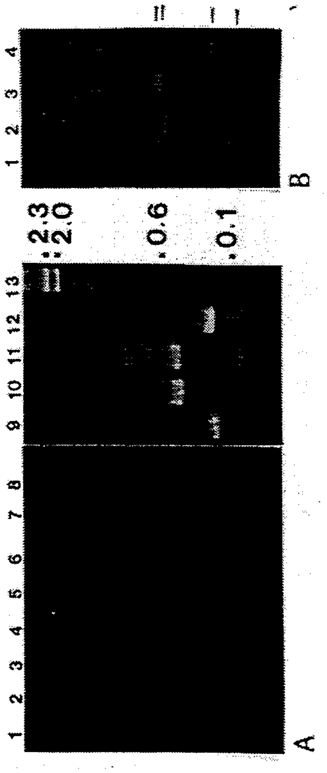
FIG. 6 shows the dependance of amplification by PCR of target DNA on the reaction buffer at two different annealing temperatures: 55° C. (A) and 60° C. (B).

Results are shown in FIG. 6: (A) lanes 1–4 represent buffer I; lanes 5–8, buffer II; lanes 9–12, buffer III. Primer pair 3/4 (SEQ ID NO:3/SEQ ID NO:4) was used for samples 1, 5 and 9; pair 4/5 (SEQ ID NO:5/SEQ ID NO:6) for samples 2, 6 and 10; pair 6/7 (SEQ ID NO:7-/SEQ ID NO:8) for samples 3, 7 and 11; pair 1/5 (SEQ ID NO:2/SEQ ID NO:6) for samples 4, 8 and 12. Annealing temperature was 55° C. In (B), the samples of lanes 9–12 were repeated with the annealing temperature of 60° C.

The size of lambda/HindIII standards (lane 13) is indicated in the margin.

EXAMPLE 9

Evaluation of Specificity of PCR Assay

Amplification of target DNA from *X. campestris* was carried out as described in Example 7 utilizing primer pair 3/4 (SEQ ID NO:3/SEQ ID NO:4). In FIG. 7(A), template DNA from pathotype A strains of *X. c. citri* from 12 countries was utilized. In 7(B), template DNA was obtained from pathotypes B and C strains of *X. c. citri* (lanes 1–5), *X. campestris* pvs. *alfalfae, bilvae* and *vignicola* (lanes 6–8), and CBSD strains of *X. campestris* (lanes 9–12).

Lane 13 contains the negative control, lane 14 contains a BRL 100 bp ladder with the lowest band of 100 bp, and the position of the predicted 222 bp amplification product is marked in the margin.

EXAMPLE 10

Evaluation of Sensitivity of PCR Assay

Detection limits of the PCR Assay for *X.c. citri* were determined utilizing purified DNA and cultured cells as samples. Amplification was carried out as described in Example 7. Southern blots were prepared using 25% of the reaction products and pFL1 as probe.

Results are shown in FIG. 8: (A) shows the detection of DNA from strain XC62 utilizing primer pair 1/5 (SEQ ID NO:2/SEQ ID NO:6). Lanes 1–8 show template DNA at 50 ng, 10 ng, 5 ng, 1 ng, 0.5 ng, 0.1 ng, 0.05 ng and 0.01 ng. DNA was detectable in an amount as low as 0.05 ng. In (B), results of a dilution end-point assay for the detection of DNA from strain XC63 utilizing primer pair 3/4 (SEQ ID NO:3/SEQ ID NO:4) are shown. A 10-fold dilution series of bacterial cells was made beginning with $2.1 \times 10^6$ cfu/10 μl (lane 1) to $2.1 \times 10^1$ cfu/10 μl (lane 6). Lanes 7 and 8 contain the positive and negative controls, respectively.

EXAMPLE 11

Detection of DNA Extracted from Leaf Lesions by PCR Assay

Immature leaves of greenhouse grown grapefruit (*Citrus paradisi*) were inoculated by placing 10-μl droplets of freshly grown *X. c citri* strain XC320 (pathotpe A, Florida, $OD_{600}=0.1$) on the leaf surface and stabbing through the inoculum droplet with a sterile needle. After seven months in the greenhouse the lesions were old and dry.

Assay samples were prepared by removing two lesions with a paper punch and grinding them together in liquid nitrogen. The DNA was extracted with a CTAB protocol at a 1/100 scale.

The PCR assay was carried out as described in Example 7 in quadruplicate using primer pairs 3/4 (SEQ ID NO:3/SEQ ID NO:4) and 1/5 (SEQ ID NO:2/SEQ ID NO:6) with a 5-μl aliquot of the extract as the source of template DNA.

Results are shown in FIG. 9 where lanes 1–4 contain DNA extracted from 4 lesion pairs; lanes 5–6 contain DNA extracted from healthy leaf controls; lanes 7 and 8 are a positive and negative ($dH_2O$) control, respectively; and lane 9 contains the 100 bp ladder mentioned in Example 9.

PCR reactions with primer pairs 3/4 (SEQ ID NO:3-/SEQ ID NO:4) and 1/5 (SEQ ID NO:2/SEQ ID NO:6) are shown in top and bottom half gels, respectively.

EXAMPLE 12

Detection of DNA from Exudate from Single Cankers by PCR Assay

Individual lesions from the leaves described in Example 11 were removed with a paper punch and minced with a razor blade in 100 μl/ml, followed by incubation at 55° C. for 12 min. Proteinase K was inactivated by a second 10-min incubation at 95° C. Samples were then incubated at 20° C. for 3 min for the addition of Amplitag polmerase (Perkin Elmer/Cetus), and amplification was carried out using primer pair 3/4 (SEQ ID NO:3-/SEQ ID NO:4), as described in Example 7.

FIG. 10 shows the results of a ten-fold dilution series from three lesions and a healthy control. In (A), the upper-half gel, lanes 1–3 and 4–6 contain DNA from lesions 1 and 2, respectively. Lane 7 is empty; lane 8 is a positive control (DNA from strain XC104); lane 9, a negative control ($dH_2O$); lane 10, a 123-bp ladder. In the lower-half gel, lanes 1–3 and 4–6 contain DNA from lesion 3 and the healthy control, respectively. Lanes 7–10 are the same as the upper-half gel.

In (B), a Southern blot of the gel shown in (A) probed with pFLI is shown.

The above-described examples demonstrate the advantages of the use of the novel probes and primers of the invention for the detection of *X.c. citri*. Specificity is improved relative to established methods. For example, serological methods have cross reactions with other strains, and all strains of *X. campestris* produce very similar pigments. In addition, a bacterium can be definitively identified as *X.c. citri* and even assigned to a subgroup based on the position of specifically detected DNA bands in a Southern blot. Speed is also improved since a single probe may be used instead of the sequential probings required by RFLP analyses.

We claim:

1. A hybridization probe effective for detecting citrus bacterial canker disease and distinguishing between citrus bacterial canker disease and citrus bacterial spot disease, said probe comprising a purified and isolated double-stranded DNA plasmid fragment which specifically hybridizes with a 4.2-kb BamHI sequence contained within plasmid DNA of *Xanthomonas campestris pv. citri*, pathotype A.

2. The hybridization probe of claim 1, wherein said probe is a 4.2-kb fragment obtained by restriction endonuclease BamHI digestion of plasmid DNA isolated from *Xanthomonas campestris* pv. *citri* pathotype A strain, or a 572-bp fragment obtained from said 4.2-kb fragment by EcoRI digestion.

3. The hybridization probe of claim 2, wherein said 572-bp fragment has the DNA sequence shown in FIG. 5 (SEQ ID NO:1).

4. The hybridization probe of claim 1, wherein said probe is cloned into a DNA vector plasmid.

5. The hybridization probe of claim 2, wherein said probe is cloned into a DNA vector plasmid.

6. The hybridization probe of claim 5, wherein the DNA vector plasmid is pUC9 and wherein the cloning of the 4.2-kb fragment results in plasmid pFL62.42 and the cloning of the 572-bp fragment results in plasmid pFL1.

7. The hybridization probe of claim 1, further comprising a detectable label wherein said label is selected from the group consisting of a radioactive, enzymatic, fluorescent, chemiluminescent and organic label.

8. The hybridization probe of claim 2, further comprising a detectable label wherein said label is selected from the group consisting of a radioactive, enzymatic, fluorescent, chemiluminescent and organic label.

9. The hybridization probe of claim 6, wherein said detectable organic label is biotin.

10. The hybridization probe of claim 7, wherein said detectable organic label is biotin.

11. An oligonucleotide primer derived from the 572-bp fragment of claim 3.

12. The oligonucleotide primer of claim 11, wherein said primer has the sequence AGA TTT TTT GCA CCC GTG (SEQ ID NO:2).

13. The oligonucleotide primer of claim 11, wherein said primer has the sequence CAC GGG TGC AAAAAA TCT (SEQ ID NO:3).

14. The oligonucleotide primer of claim 11, wherein said primer has the sequence TGG TGT CGT CGC TTG TAT (SEQ ID NO:4).

15. The oligonucleotide primer of claim 11, wherein said primer has the sequence TGT CGT CGC TTG TAT GGC (SEQ ID NO:5).

16. The oligonucleotide primer of claim 11, wherein said primer has the sequence GAC CGT TCA GGA GTT GGG (SEQ ID NO:6).

17. The oligonucleotide primer of claim 11, wherein said primer has the sequence ATG GCG TTG GTG TCG TCG (SEQ ID NO:7).

18. The oligonucleotide primer of claim 11, wherein said primer has the sequence GGG TGC GAC CGT TCA GGA (SEQ ID NO:8).

19. A method of detecting *Xanthomonas campestris* pv. *citri* (*X.c. citri*), said method comprising a. providing a test DNA sample obtained from a bacterium suspected of being *X.c. citri*, b. contacting said sample with a probe which specifically hybridizes with a 4.2-kb BamHI sequence contained within plasmid DNA of *X.c. citri*, pathotype A, and c. detecting the presence of hybridized DNA, as an indication of the presence of *X.c. citri*.

20. The method of claim 19, wherein said probe is a 4.2-kb fragment obtained by restriction endonuclease BamHI digestion of plasmid DNA isolated from *Xanthomonas campestris* pv. *citri* pathotype A strain, or a 572-bp fragment obtained from said 4.2-kb fragment by EcoRI digestion.

21. The method of claim 19, wherein said probe is plasmid pFL62.42 or plasmid pFL1.

22. The method of claim 19, wherein said probe comprises a detectable label wherein said label is selected from the group consisting of a radioactive, enzymatic, fluorescent, chemiluminescent and organic label.

23. The method of claim 22, wherein said organic label is a biotin label.

24. A method of detecting *Xanthomonas campestris* pv. *citri* by polymerase chain reaction, said method comprising a. providing a test sample suspected of containing the DNA of bacterium *Xanthomonas campestris* pv. *citri*, b. amplifying said DNA with primer pairs selected from the group consisting of SEQ ID NO:2, SEQ ID NO:3, SEQ ID NO:4, SEQ ID NO: 5, SEQ ID NO: 6, SEQ ID NO: 7 and SEQ ID NO: 8, wherein said amplifying is carried out in buffer comprising 50mM Tris-HCl, 20mM NaCl, 3mM $Mg^{2+}$, 1% Triton X-100, and 0.1% gelatin, having a pH of about 9.0, c. detecting the presence of amplified DNA as an indication of the presence of *Xanthomonas campestris* pv. *citri*.

* * * * *